United States Patent [19]
Bath

[11] Patent Number: 5,919,186
[45] Date of Patent: *Jul. 6, 1999

[54] LASER APPARATUS FOR SURGERY OF CATARACTOUS LENSES

[76] Inventor: Patricia E. Bath, 4554 Circle View Blvd., Los Angeles, Calif. 90043

[ * ] Notice: This patent is subject to a terminal disclaimer.

[21] Appl. No.: 08/854,138

[22] Filed: May 8, 1997

Related U.S. Application Data

[63] Continuation of application No. 07/717,794, Jun. 19, 1991, which is a continuation of application No. 07/159,931, Feb. 24, 1988, which is a division of application No. 06/943,098, Dec. 18, 1986, Pat. No. 4,744,350.

[51] Int. Cl.⁶ ...................................................... A61N 5/06
[52] U.S. Cl. ...................................... 606/6; 606/3; 606/10; 606/15
[58] Field of Search .................................. 606/3–6, 10–18

[56] References Cited

U.S. PATENT DOCUMENTS

| | | |
|---|---|---|
| 3,433,226 | 3/1969 | Boyd . |
| 3,971,383 | 7/1976 | Krasnov . |
| 3,982,541 | 9/1976 | L'Esperance, Jr. . |
| 4,320,761 | 3/1982 | Hoddad .................................. 604/22 |
| 4,538,608 | 9/1985 | L'Esperance ............................ 606/5 |
| 4,583,539 | 4/1986 | Karlin et al. ............................ 606/4 |
| 4,686,979 | 8/1987 | Gruen et al. . |
| 4,694,828 | 9/1987 | Erchenbaum ............................ 606/6 |
| 4,744,360 | 5/1988 | Bath . |
| 5,324,282 | 6/1994 | Dodick . |
| 5,334,183 | 8/1994 | Wuchinich . |

OTHER PUBLICATIONS

C. Davis Belcher III, "The Future", *Ophthalmic Laser Therapy*, vol. 2, No. 4, 1987.
C. Davis Belcher III, "Phacoablation", *Ophthalmic Laser Therapy*, vol. 3, No. 1, 1988.
Gailitis et al., "Comparison of Laser Phacovaporization . . . ", '78/SPIE vol. 1744, *Ophthalmic Technologies II* (1992).

*Primary Examiner*—David M. Shay

[57] ABSTRACT

A method and apparatus for removing cataracts in which a flexible line preferably 1 mm or less in diameter is inserted through an incision into the anterior chamber until its end is adjacent the cataract. Coherent radiation, preferably at a frequency between 193 and 351 nm, is coupled to the cataract by an optical fiber in the line. An irrigation sleeve provided about the fiber and an aspiration sleeve extending partially around the irrigation sleeve conduct irrigating liquid to and remove ablated material from the anterior chamber and form with the optical fiber the flexible line.

17 Claims, 1 Drawing Sheet

LASER APPARATUS FOR SURGERY OF CATARACTOUS LENSES

This is a continuation of the application Ser. No. 07/717,794 filed Jun. 19, 1991, which is a continuation of Ser. No. 07/159,931, filed Feb. 24, 1988, which is a divisional of Ser. No. 06/943,098, filed Dec. 18, 1986, now U.S. Pat. No. 4,744,350.

BACKGROUND AND SUMMARY OF THE INVENTION

The invention relates to a method and apparatus for coupling laser radiation to a cataract lens in the eye to ablate the same.

Every eye is divided into an anterior and posterior chamber separated by a normally transparent lens which focuses light onto the retina at the back of the posterior chamber. When the lens becomes cloudy for any of a variety of reasons sight is impaired and the cloudy lens must be removed. Following removal of the lens, an intraocular lens (IOL) implant can be placed in the posterior chamber or thick glasses or contact lenses used to focus the light.

A number of techniques are now in use for this common surgical procedure. An incision can be made in the eye and a sharp instrument inserted to cut and then aspirate by vacuum the cloudy cataract tissue. More recently, a small incision-typically 3 mm-can be made in the eye surface and an ultrasonic probe inserted to a position adjacent to the lens. The ultrasonic energy then disintegrates the lens material which can likewise be removed by aspiration.

Laser radiation is now used widely in various surgical techniques particularly those involving the eye. For example, the patent to Krasnov, 3,971,382, describes a technique in which laser radiation is focused onto the anterior capsule of the lens to form a hole through which the cataract substance can be drawn from the lens capsule.

Optical fibers are also commonly used for medical and other applications to transmit coherent radiation from a laser to some location in the body where material is to be coagulated or disintegrated. U.S. patent application Ser. No. 702,569, filed Feb. 19, 1985, describes a micro instrument with an optical fiber. The optical fiber can be inserted into the eye for the removal of abnormal tissue such as tumors. Radiation with a wavelength between 200 and 400 nm is said to be appropriate.

The present invention relates to a method and apparatus in which coherent radiation is transmitted by a flexible line containing an optical fiber is inserted through a limbel incision, preferably 1 mm or less, in the eye surface and then through a 1 mm or less anterior capulotomy into the lens nucleus. The optical fiber is then positioned within the crystalline lens.

Coherent radiation disintegrates the crystalline material into extremely small particles less than 0.1 mm in diameter. These nuclear particles and cortex can then be irrigated and aspirated from the capsular bag, which is left intact, except for the 1 mm anterior capsulotomy, via an aspiration sleeve which is formed about and extending along the optical fiber. At the same time irrigating liquid is supplied via an irrigation sleeve likewise formed about and extending along the optical fiber.

Since the particles produced by this ablation are so small, the device can be made to be extremely small and therefore, the incision likewise can be made much smaller than with other techniques such as ultrasonic. Utilizing an optical fiber further permits the energy to be more efficiently and effectively focused onto the lens to be removed.

Radiation in the range of 193 to 351 nm has proved to be satisfactory. In particular, 308 nm was found to be the most effective experimental wavelength. However, the invention is also effective at other wavelengths, for example, between 193 nm and 3000 nm.

DETAILED DESCRIPTION OF THE PREFERRED EMBODIMENT

Figure 1:
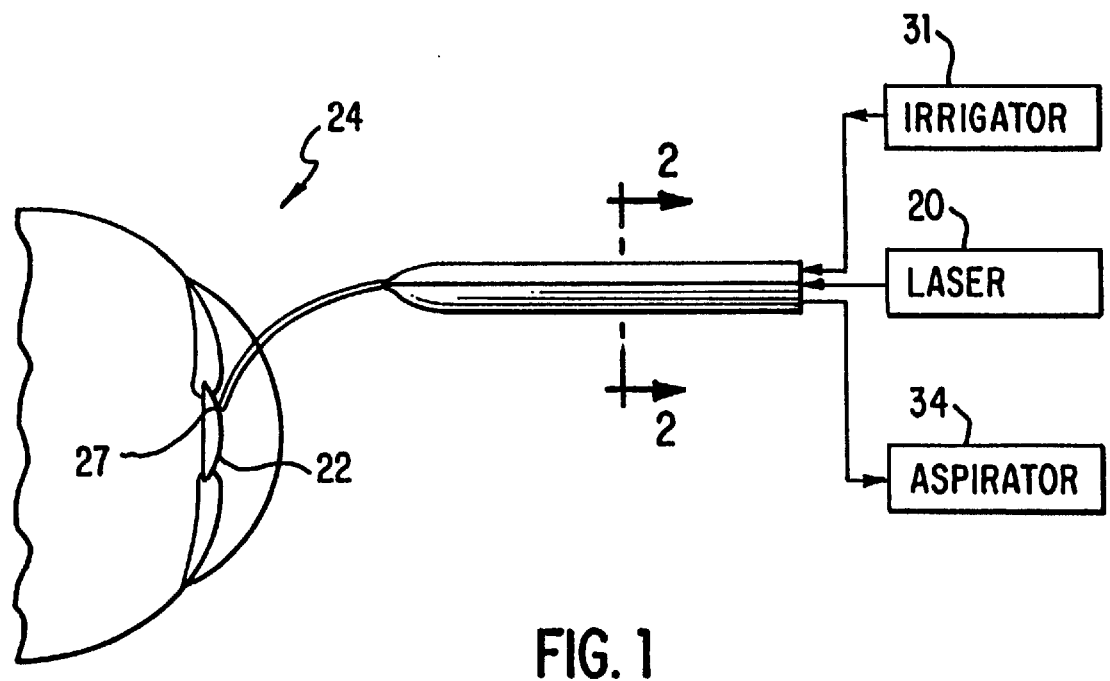
FIG. 1 shows a schematic view of the present invention being used for ablating a cataract lens.
Figure 2:
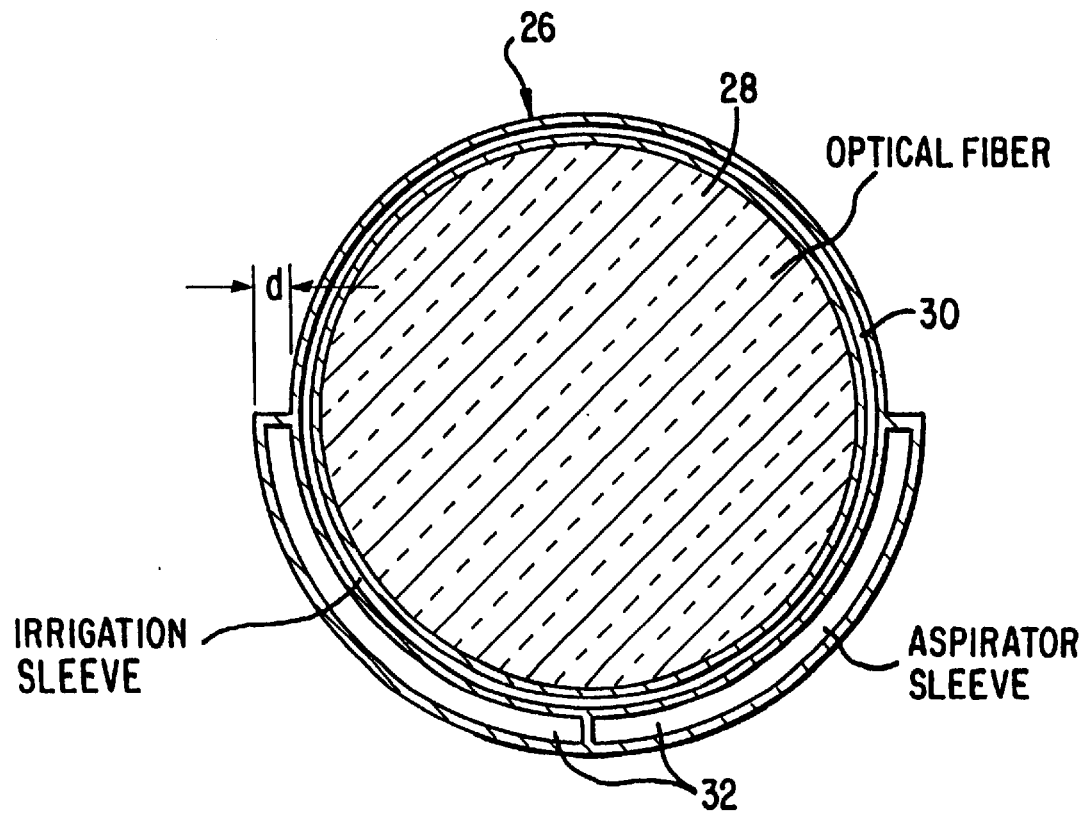
FIG. 2 shows a cross-section of the flexible line of FIG. 1 along the lines 2–2.

Reference is now made to FIGS. 1 and 2 which illustrate a preferred embodiment of the present invention. First, a flexible line 26 is introduced into the interior of the lens nucleus through a 1 mm limbel incision and a 1 mm anterior capsulotomy. Pulsed excimer coherent radiation from a suitable and conventional laser 20 at a suitable energy is coupled to the interior aspect of a cataract lens 22 in a human or animal eye 24 by a flexible line 26 until the desired amount of ablation occurs.

As can be best seen in FIG. 2, flexible line 26 is formed of a conventional optical fiber 28 suitable for medical applications, for example, quartz silica. The line is then directed successively to the inferior, central and superior areas of the lens nucleus and phakoablation again performed at each area. An irrigation sleeve 30 surrounds the optical fiber and is connected to a suitable irrigation device 31 for supplying irrigating liquid to the eye during surgery at a suitable pressure. Aspiration sleeve 32 extends partially around the irrigation sleeve and is likewise coupled to a conventional aspirator 34 for removing by an appropriate suction the minute particles of cataract tissues which are produced in response to incidence of the coherent radiation.

The wavelength of the radiation is preferably in the range as set forth above. Since the particles are so small, the width d of the aspiration sleeve can be 0.3 mm or less. The optical fiber can be made to be no more than 600 microns in diameter and the aspiration sleeve similarly no more than 0.1 mm so that the entire flexible tube 26 can be made of a diameter no greater than 1 mm, permitting the size of the incisions to be minimized.

EXAMPLE

A Lambda Physik 102 Xenon Chloride Excimer laser operating at 308 nm was utilized for these experiments. The laser had unstable resonator optics and rectilinear output aperture producing a 2.2×0.7 beam. The maximum output of the laser was 250 mj. The laser output travelled through a 7 mm hole and was then focused by a quartz lens and optical delivery system which transmitted the optical radiation to the optical fiber (400 mm focal length). The pulse length was 17 nanoseconds and the maximum rep rate was 100 Hertz. By moving the lens, a variation in light flux could be produced. Prior to each irradiation event the pulse energy was measured with a Genetic joulemeter.

Prior to performing ablation the thresholds for ablation of lens nucleus and cortex and bovine lenses was determined.

The target consisted of whole bovine lenses or human lenses with intact lens capsules. Bovine lenses were obtained from freshly enucleated globes using standard microsurgical intracapsular technique. The bovine lenses measured 1 cm in sagittal section, i.e., distance from anterior capsule to posterior capsule. Lenses were tested within 4–8 hours of enucleation.

Human lenses were obtained from freshly enucleated cadaver eyes, preserved by standard moist chamber storage. After excision of the cornea, lenses were delivered using intracapsular microsurgical technique and tested within 12–36 hours post mortem.

Whole lenses were mounted in a 16 mm fixation ring which had a 5 mm aperture. Two methods were utilized to determine the ablation rates. The first method was used for the determination of the ablation rate for the cortex. The entire lens was mounted in the fixation ring and holes were drilled at different energy values, a maximum of 2 mm in the lens. This is essentially equivalent to insertion of an optical fiber during surgery as described above.

For the case of cortex, ablation was essentially absent at energy densities below 7 $mj/mm^2$. In the case of bovine nucleus, the ablation threshold was approximately 10 $mj/mm^2$.

At an energy density of 22 $mj/mm^2$, the ablation rates for bovine cortex and nucleus were 6 microns/pulse and 13 microns/pulse respectively.

At an energy density of 53 $mj/mm^2$, the ablation rates for bovine cortex and nucleus were 42 microns/pulse and 23 microns/pulse, respectively. These differences were statistically significant at the 0.05 level.

The ablation threshold was determined to be approximately 3 $mj/mm^2$. At an energy density of 22 $mj/mm^2$ the ablation rate was approximately 10 microns/pulse. And at energy density of 40 $mj/m^2$ the ablation rate was approximately 40 microns/pulse.

Many changes and modifications of the above described embodiment of the invention can be carried out without departing from the scope of the invention. Accordingly, that scope is intended to be limited only by the scope of the appended claims.

What is claimed is:

1. An apparatus for surgically removing a cataract from the posterior chamber of a human or mammal's eye, by using a laser, which laser applies pulse energy to the cataract, wherein the cataract is in a cataractous crystalline lens that includes a lens nucleus of crystalline material in which the cataract is formed covered by a cortex, the cataractous crystalline lens being disposed within a capsular bag in the posterior chamber of the eye, said apparatus comprising:

a) Means for making incisions into an anterior chamber and a capsular bag
   b) Means for passing an end of a line including an optical fiber through said incision, said optical fiber having a first unshielded distal end and a second opposite end, said optical fiber having a laser optically coupled to said opposite second end;
   c) Means for positioning said unshieled distal end of said optical fiber adjacent to the cataract so that said unshielded distal end is adjacent the cataractous crystalline lens.
   d) Means for energizing said optical fiber with short pulses to a predetermined threshold level sufficient to ablate the crystalline material of the lens nucleus into particles and
   e) Means for irrigating with a liquid the lens being ablated and means for aspirating the liquid with the lens particles entrained therein to remove the crystalline material and thus the cataract from the eye by applying suction to the liquid.

2. The apparatus of claim 1, wherein said laser energizes said optical fiber with coherent radiation in the range of 193 nm to 3000 nm.

3. The apparatus according to claim 1, said optical fiber is a flexible optical fiber.

4. The apparatus according to claim 1 wherein said unshielded distal end of said optical fiber is positioned adjacent to the lens nucleus of the crystalline lens having inferior, central and superior zones.

5. The apparatus of claim 1, said optical fiber is solid.

6. The apparatus of claim 1, said optical fiber is a single strand.

7. The apparatus of claim 1, producing ultrashort pulses in the nanosecond range.

8. The apparatus according to claim 1 wherein said means for irrigating and said means for aspirating the lens being ablated conveys liquid to and away from the lens along an axis of said line which is coextensive with a longitudinal axis of said optical fiber.

9. The apparatus of claim 8 wherein said means for irrigating includes an annular tube extending coaxially with said optical fiber.

10. The apparatus of claim of claim 9 wherein said means for aspirating liquids away from the lens includes a tube adjacent to said annular tube.

11. The apparatus according to claim 1, further including means for measuring the pulse energy of said laser prior to energizing said optical fiber.

12. The apparatus according to claim 11 wherein said optical fiber is energized with coherent radiation in the range of 193 nm to 3000 nm.

13. The apparatus of claim 12 wherein said means for irrigating and said means for aspirating the lens being ablated conveys liquid to and away from the lens along an axis of said line which is coextensive with a longitudinal axis of said optical fiber.

14. The apparatus according to claim 13 wherein said means for irrigating includes an annular tube extending coaxially with said optical fiber.

15. The apparatus according to claim 14 wherein said means for aspirating the lens particles includes a tube adjacent to said annular tube.

16. The apparatus of claim 15, said optical fiber is solid.

17. The apparatus according to claim 15, said optical fiber is a single strand.

* * * * *